United States Patent [19]

Ishida et al.

[11] 4,288,550
[45] Sep. 8, 1981

[54] TREATING PROCESS OF GARBAGE CONTAINED WASTES

[75] Inventors: Masahiko Ishida; Ryoichi Haga; Yoji Odawara, all of Hitachi, Japan

[73] Assignee: The Agency of Industrial Science and Technology, Tokyo, Japan

[21] Appl. No.: 956,724

[22] Filed: Nov. 1, 1978

[30] Foreign Application Priority Data

Nov. 8, 1977 [JP] Japan ............................... 52-133017

[51] Int. Cl.³ .............................................. C12P 5/02
[52] U.S. Cl. .................................... 435/167; 435/161; 435/163; 435/247; 435/801; 435/921; 435/940; 48/197 FM
[58] Field of Search ................. 195/27, 29.13, 30, 33, 195/49, 82, 96, 111; 210/2, 11, 16, 12; 426/53, 13; 48/197 R, 197 FM; 435/161, 162, 163, 165, 247, 249, 250, 166, 921, 928, 940, 801

[56] References Cited

U.S. PATENT DOCUMENTS

| | | | |
|---|---|---|---|
| 2,085,003 | 6/1937 | Christensen et al. | 435/165 |
| 2,182,989 | 12/1939 | Jean | 435/163 |
| 3,383,309 | 5/1968 | Chandler | 195/96 |
| 3,769,437 | 10/1973 | Pour-El | 426/11 |
| 3,787,583 | 1/1974 | Hruby | 426/53 |
| 3,972,775 | 8/1976 | Wilke et al. | 435/163 |
| 3,994,780 | 11/1976 | Klass et al. | 195/33 X |
| 4,022,665 | 5/1977 | Ghosh et al. | 195/127 |
| 4,040,953 | 8/1977 | Ort | 195/33 X |
| 4,094,740 | 6/1978 | Lang | 195/127 |

OTHER PUBLICATIONS

Laskin et al. "Handbook of Microbiology" vol. III Microbial Products CRC press (1976) pp. 655–656.
Lodder "The Yeasts" North Holland Publishing Co. (1970) pp. 619–620.
Tamaoki "Alcohol by Fermentation" Chemical Abstract No. 69147x (1974) p. 220.
Rose et al. "The Yeasts" Physiology & Biochemistry of Yeasts" vol. 2 (1971) Academic Press pp. 31, 55.

*Primary Examiner*—R. B. Penland
*Attorney, Agent, or Firm*—Birch, Stewart, Kolasch & Birch

[57] ABSTRACT

The present invention relates to a process for digesting garbage or garbage contained wastes, particularly to a microbiological treatment which facilitates the treatment with high efficiency and economics, for the recovery of methane gas, first, by effecting an alcohol fermentation treatment by alcohol fermentative yeasts which can directly convert starch into ethanol without a starch hydrolysis pretreatment in the slurry state, followed by a direct methanization by methane bacteria of the fermented product containing ethanol, without effecting sterilization treatment of garbage or garbage contained wastes.

9 Claims, 1 Drawing Figure

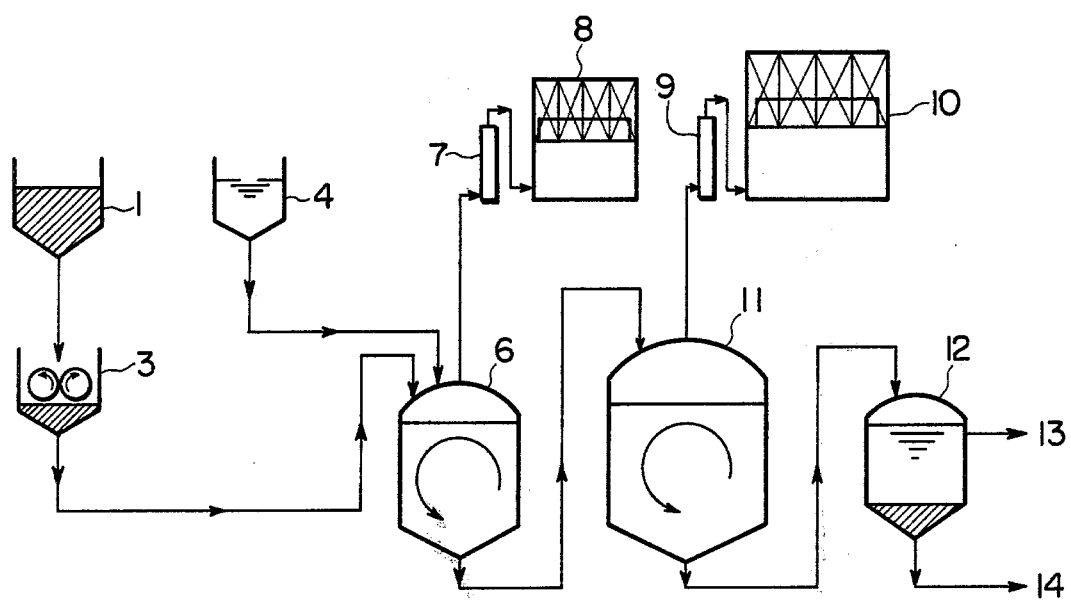

TREATING PROCESS OF GARBAGE CONTAINED WASTES

BACKGROUND OF THE INVENTION

The present invention relates to a process for digesting garbage or garbage contained wastes, particularly to a microbiological treatment which facilitates the treatment with high efficiency and economics.

Although presently garbage and garbage contained wastes are being incinerated or reused for land reclamation, they are causing various secondary pollution troubles, as it is well known.

In this regard, such organic wastes as excess activated sludge and human wastes have so far been treated by an anaerobic digestive method. Recently, however, there is an indication that even garbage contained wastes are to be treated by an anaerobic digestive method. This anaerobic digestive method possesses such advantages as that it enables a reuse of the by-product methane gas as energy for operating the digestion facilities, and that it enables an effective use of digested sludge as a useful organic fertilizer. On the other hand, as a mechanism of anaerobic digestion, mainly two reactions are known. Namely, one is a liquefaction reaction wherein such volatile fatty acids as acetic acid, propionic acid and n-butyric acid are obtained by turning the organics involved in waste water into low molecular weight substance through the action of anaerobic liquefaction bacteria (septic bacteria), and the other is a reaction wherein these fatty acids thus produced are converted into methane by the action of gasification bacteria (methane bacteria). Thereagain, the usually exercised anaerobic digestion follows a process wherein the treatment is performed under a coexistent state of these two bacteria groups in the same tank for an extended period of time as long as 30 to 50 days. On account of this, in spite of such aforementioned non-polluting and energy-saving characteristic features, its actual application has been declining in number from year to year, to the extent where it is presently employed only for treating human wastes a few other purposes.

Quite recently, its aforementioned advantageous points are being re-evaluated, and studies are progressing in the U.S.A. and some other countries, in order to improve its low treatment efficiency which is the primary drawback of the process. Lately, it has been evidenced that the above two reactions can be separated from each other, and it is possible to shorten the treatment period significantly from that of the conventional parallel-dual fermentation by optimizing each of these two reactions. Incidentally, however, under the aforementioned two-step treatment process, the liquefaction reaction at the first step proceeds within a state of a weak acidic to neutral pH, but, because of the conversion of organic substances into volatile fatty acids in the course of the treatment process, it necessitates an amount of alkali, as a neutralizer, almost equivalent to the volume of organic acid generated. Any use of neutralizer in the course of the liquefaction process results in a lower separability of digested sludge and separated water at the final step. Moreover, if garbage is treated at the liquefaction process of the first step, sometimes it generates hydrogen gas in addition to carbon dioxide, and the volume of the generated hydrogen gas, in some cases, reaches 0.1 $m^3$ per each kg of the charged organics. If the hydrogen gas is generated at the liquefaction process of the first step, much chemical energy would be lost at the liquefaction process, and it naturally affects the methane yield at the gasification of the second step.

SUMMARY OF THE INVENTION

The purpose of the present invention is to eliminate the aforementioned defects of the conventional technique and to make available a highly efficient and economic treatment process.

Furthermore, the characteristic feature of the present invention is to use alcohol fermentation, as described hereunder, which is to be exercised in lieu of the liquefaction process of the aforementioned two-step liquefaction treatment method; that is, to convert the fermentable carbohydrate into ethanol by alcohol fermentative yeast in the liquid state, without sterilizing organic wastes, and, next, to recover methane gas by treating the fermented product which contains ethanol directly with methane bacteria. In this manner, the fermentable carbohydrate contained in garbage can be turned with a better yield into an energy source of methane bacteria and carbon source. This process avoids a voluminous generation of hydrogen gas as was encountered in the conventional liquefaction process (acidic fermentation) and also permits the reduction of the required volume of neutralizer down to 10–20% of the conventional process.

Further, in exercising the aforementioned alcohol fermentation treatment, it is preferable to exercise it under a co-existent state with amylase producing yeasts, lipase producing yeasts and protease producing yeasts in addition to alcohol fermentative yeasts; that is, simultaneously to further lower the molecular weight of undecomposed starch contained in garbage in order to accelerate the activity of the alcohol fermentative yeast, and to change the ingredients into a state which facilitates the activity of gasification bacteria which come into action at the next step, by turning the ingredients of fat, protein, etc. effectively into low molecular weight substances.

BRIEF DESCRIPTION OF THE DRAWING

FIG. 1 is the flow-sheet related to one example of the present invention.

DESCRIPTION OF THE PREFERRED EMBODIMENT

An example of the organic wastes digestion process of the present invention is illustrated in the drawing, with the detailed explanation made hereunder in the order of each step.

First, the garbage or garbage contained wastes 2 which are stored in feedstock storage tank 1 are pulverized by crusher 3. Of course, if it does no harm the slurry transmission and stirring within the tanks at the steps to follow, this crushing process could be omitted. Next, water supplied from water tank 4 is added to the crushed garbage slurry if required to make the solids concentration in the slurry to 5–20%. Next, the slurry is charged into alcohol fermentation tank 6 and treated under a mix-cultured state of alcohol fermentation yeast, amylase producing yeasts, lipase producing yeasts and protease producing yeasts. Yeasts having strong alcohol fermentation activity such as Saccharomyces Genus (*S. cerevisiae S. carlsbergensis*), Schizosaccharomyces Genus (*Schizosaccharo-myces pombe*), Schwaniomyces Genus, Torulopsis Genus (*T. dattila*), Brettanomyces Genus, Candida Genus (*C. Krusei*), etc. are used as the alcohol fermentative yeast. As for amylase producing yeasts, *Endomycopsis fibuliger, Schizosaccharomyces pombe, Saccharomyces diastatics*, etc. are used. As for protease producing yeasts, *Candida lipolitica, Candida parapsilosis*, etc. are used, and, as for lipase producing yeasts, *Candida cylindracea, Candida lipolitica, Trichosphoron pullulens*, etc. are used.

To treat with the aforementioned microorganisms, the slurry is kept stirred at a certain fixed temperature for several days, under an anaerobic condition. By this fermentation treatment, the carbohydrate contained in garbage is turned into alcohol, and the contained fat and protein are turned into lower molecular weight substances respectively. The temperature employed for fermentation is in the range of 20°–40° C., and it can be conveniently selected according to the microorganisms used and their combination. In case the pH decreases in the course of fermentation, it is necessary to add neutralizer so as to adjust it to the range of pH 4–6.5. As for neutralizer, slaked lime, calcium carbonate, and other alkaline materials containing lime, for instance, carbide residue can be used. As for stirring and maintenance of the temperature, the methods which have been employed in the conventional anaerobic digestion process are applied. The gas generated from the alcohol fermentation tank contains over 95% carbon dioxide, other than this, nitrogen, hydrogen and a trace of hydrogen sulfide. This gas is stored in gas storage tank 8, after eliminating hydrogen sulfide therefrom at desulfurizer 7. The slurry from the alcohol fermentation is charged into gasification tank 11, and low molecular substance which is mainly ethanol is converted into methane and carbon dioxide, by coming into contact with gasification bacteria (methane bacteria). For this gasification treatment to progress with satisfactory efficiency, it is required to keep up the temperature at the range of 20°–75° C. under an anaerobic condition and adjust pH to 7–8. As for gasification bacteria, those which have so for been in use, such as Methanosaricina Genus, Methanococcus Genus, Methanobacterium Genus, etc., can well be used. The main ingredients of the generated gas are methane 60–85% and carbon dioxide 15–40%, and further small amounts of nitrogen, hydrogen and hydrogen sulfide are also involved. The generating gas is stored in gas storage tank 10, after hydrogen sulfide is removed by desulfurizer 9. Following gasification the slurry is lead into solids/liquid separation tank 12 for the final treatment where it is separated to separated water 13 and digestive sludge 14.

The following Examples are given as illustrative of the present invention.

EXAMPLE 1

A slurry of 10% organic concentration (solids concentration 12%) was prepared by adding water to garbage contained wastes (garbage content: dry waste 70%, water 50% and) crushed by a pulverizer. Three kg of the aforementioned slurry was mixed with 0.5 kg of seed culture prepared in advance by mix-culturing *Saccharomyces Cerevisiae Saccharomyces diasbtitics and Candia lipolitica* under an anaerobic condition at pH 5 and 30° C. for 3 days, and this mixture was charged into a cylindrical stainless steel container of 5l effective capacity equipped with a stirrer, jacket and a pH adjusting system.

Next, the mixture therein was processed through a liquefaction fermentation treatment by stirring at 100 rpm and at 30° C. and pH 5.0 for 3 days, then from the 4th day onward a continual charging was effected at organics load of 25 g - dried organics/d. At the end of the 10th day from commencement of a continual charging, the alcohol concentration of the slurry was 3.0% (W/W) and the generated gas volume was 16 Nl/kg-slurry (carbon dioxide 95 vol %, hydrogen 2 vol %, others 3 vol %), and the volume of slaked lime required for neutralization was 1.1 g/kg-slurry.

Next, the slurry treated by the aforementioned fermentation treatment was transferred into a gasification tank of a 20l effective capacity at the rate equal to the discharging velocity from the liquefaction tank, and a gasification treatment was conducted therewith. The gasification tank has a stirrer, jacket and an automatic pH adjusting system the same as the liquefaction tank. The gasification wasexercised under the conditions of slurry volume within the tank of 10.5l, residence time of 12 days and at 60° C. and pH 7.8. As for the gasification seed culture, the slurry used was the digested garbage contained slurry subjected, in advance, to the liquefaction treatment under the same conditions as aforementioned under the anaerobic conditions at pH 7.6 and 30° C. for 10 days. The gas generation from the gasification tank was 35 N l/kg-slurry (methane concentration 75 vol%) at the end of 10 days after commencement of continual charging, of which mathane was 26.3 N l/kg-slurry and carbon dioxide was 8.7 n l/kg-slurry.

COMPARATIVE EXAMPLE 1

As a reference against Example 1, the following experiment was performed.

A slurry of organics concentration 10 wt% (solids concentration 12 wt %) was prepared by adding water to the garbage contained wastes taken from the identical batch of the starting material of the aforementioned Example 1 and crushed by a pulverizer. Three kg of the aforementioned wastes slurry and 0.5 kg of seed culture prepared in advance by mix-culturing the aforementioned wastes slurry and volatile fatty acid producing bacteria (liquefaction fermentation bacteria) at pH 5.8 and 60° C. under an anaerobic condition were charged into a liquefaction tank with the specifications identical to the tank employed in Example 1. Next, batchwise fermentation was exercised with in-tank slurry volume of 3.5l, with stirring at 100 rpm, at 60° C. and pH 5.8 for 3 days. After completion of fermentation, a continual charging at the rate of garbage contained wastes of 875 g/d (organics load: 25 g-dried organics/l.d) and a residence time of 4 days was mode. At the same time a continual discharge equivalent to the charged volume was made. At the end of 10 days after commencement of the continual charging, volatile fatty acid concentration within the slurry was 3.2 wt % (n-butyric acid 1.9%, acetic acid 1.1%, other fatty acids 0.2%), and the generated gas volume was 19.3 Nl/kg-slurry (carbon dioxide 55 vol %, hydrogen 45 vol %), and the volume of slaked lime required for adjustment of pH in the course of fermentation was 20.1 g/kg-slurry.

Next, a continual gasification treatment was performed by charging the slurry subjected to the liquefaction fermentation treatment into the gasification tank having the identical specifications to the one used in Example 1 with the charging rate idential to that of the discharging slurry from the liquefaction tank. The gasification fermentation treatment was exercised under the conditions of the liquid volume within the tank of 10.5l, residence time of 12 days, stirring speed of 100 rpm., liquid temperature of 30° C. and pH of the liquid of from 7.4 to 7.6. As for the seed culture for gasification fermentation, the slurry used was the digested garbage contained slurry subjected, in advance, to the liquefaction treatment under the same conditions as aforementioned under anaerobic conditions at pH 7.6 and 60° C. for 10 days. The generated gas volume at the end of 10 days after commencement of the continual charging was 32.9 Nl/kg-slurry (methane concentration 70 vol %) of which methane was 22.4 Nl/kg-slurry and carbon dioxide was 9.7 Nl/kg-slurry.

Comparing Example 1 with Comparative Example 1, by applying the present invention the recovered volume of methane was improved by 18% as against Comparative Example 1 and the methane concentration was increased to 75 vol % as against the 70 vol % of Comparative Example 1. Furthermore, by the present invention the volume of slaked lime consumed at the time of liquefaction fermentation for each 1 kg of the wastes slurry was reduced by 95% as compared with Comparative Example 1.

EXAMPLE 2

After mixing 20 kg of water with 20 kg of garbage wastes (water content 75 wt %), and by mixing this mixture by a home mixer for 2 minutes, a slurry of solids concentration 12.5 wt % and organics concentration 9.8 wt % was prepared.

Next, 0.5 kg of a liquefied seed culture prepared by mix-culturing in advance 1.5 kg of the garbage wastes of the identical batch to the aforementioned garbage wastes and four kinds of yeast of Saccharomyces Carlsbergensis, Schizosaccharomyces pombi, Candida parapsilosis and Candida cylindracia was charged into a cylindrical acrylic plastic fermentation tank of a 2l capacity equipped with a stirrer, jacket, and an automatic pH adjusting system.

The resultant mixture was subjected to a liquefaction fermentation treatment for 3 days by stirring at 100 rpm, at 30° C. and pH 5.0-5.4. For guidance, the aforementioned seed culture was prepared by mixing 2 kg of the garbage wastes taken from the batch identical to the aforementioned one and the aforementioned four kinds of yeast and by subjecting it to a fermentation treatment at pH 5.0-5.4 and 30° C. with stirring at 100 rpm for 4 days. The alcohol concentration in the aforementioned liquefied/fermented slurry was 2.3 wt % and the generated gas volume was 10.7 Nl/kg-slurry (carbon dioxide 98 vol %, hydrogen 1.5 vol %, others 0.5 vol %). The slaked lime required for adjusting the pH in the course of fermentation was 2.2 g/kg-slurry.

Next, by charging 0.5 kg of the aforementioned liquefied/fermented slurry and 1.5 kg of the seed culture for gasification fermentation treatment into a fermentation tank of a 2l capacity with the identical specifications to that used for the aforementioned liquefaction fermentation treatment, a batchwise gasification fermentation treatment was performed at pH 7.6-7.8 and 30° C. and with stirring at 70 rpm for 10 days. The gasification seed culture, used was prepared from the mixture of the garbage wastes slurry of the identical batch to the aforementioned one and middle temperature methane bacteria which were both charged into a 20l acrylic plastic fermentation tank and cultured under an anaerobic condition at 30° C. and pH 7.6-7.8 for 1 month. The generated gas volume in the course of a 10 day fermentation was 36.9 Nl/kg-slurry (methane purity 90 vol%), of which methane was 33.2 Nl/kg-slurry, carbon dioxide 3.7 Nl/kg-slurry.

EXAMPLE 3

1.5 kg of garbage slurry from the identical batch which was used for Example 2 (organics concentration 9.8 wt %) and 0.5 kg of the liquefaction seed culture which was prepared in advance by mix-culturing four kinds of yeasts of Candida Krusei, Endomycopsis filubiger, Candida parapilosis and Trichosporon pullulens was charged into a cylindrical acrylic plastic fermentation tank of 2l effective capacity equipped with a stirrer and jacket and an automatic pH adjusting system and was subjected to a liquefaction fermentation treatment with stirring at 100 rpm for 3 days at 30° C. and pH 5.0-5.4. For guidance, the aforementioned liquefaction seed culture was prepared by adding the aforementioned four kinds of yeasts to 2 kg of the garbage slurry of the identical batch as the aforementioned one and fermented with stirring at 100 rpm at 30° C. and pH 5.0-5.4 for 4 days. The alcohol concentration in the aforementioned slurry liquefied/fermented for 3 days was 2.8 wt %, and the generated gas volume was 13.0 Nl/kg-slurry (carbon dioxide 96 vol %, hydrogen 3 vol %, others 0.4 vol %). The slaked lime required for adjusting the pH during fermentation was 2.5 g/kg-slurry.

Next, 0.5 kg of the aforementioned liquefied slurry and 1.5 kg of the seed culture for gasification fermentation were charged into a 2l fermentation tank with the identical specifications to the one which was used for the aforementioned liquefaction treatment, and a batchwise gasification fermentation was effected withstirring at 70 rpm for 10 days at 60° C. and pH 7.6-7.8. The gasification seed culture used was prepared by culturing the garbage slurry from the identical batch to the aforementioned one and middle temperature gasification fermentation bacteria (middle temperature methane bacteria) in a 20l acrylic plastic fermentation tank under an anaerobic condition at 60° C. and pH 7.6-7.8 for over 1 month. The volume of gas recovered at the end of fermentation was 39.0 Nl/kg-slurry (methane purity 89.5 vol %), of which methane was 35.4 Nl/kg-slurry and carbon dioxide 3.6 Nl/kg-slurry

EXAMPLE 4

1.5 kg of garbage slurry from the batch identical to the one used for Example 2 (organics concentration 9.8 wt %) and 0.5 kg of liquefaction seed culture obtained by mix-culturing in advance two kinds of yeasts of Saccharomyces cerevisiae and Saccharomyces diastatics were charged into a 2l effective capacity cylindrical acrylic plastic fermentation tank equipped with a stirrer, jacket and an automatic pH adjusting system and subjected to a liquefaction fermentation treatment with stirring at 100 rpm, at 30° C. and pH 5.0-5.4 for 3 days. The aforementioned liquefaction seed culture was prepared through fermentation treatment of the garbage slurry from the batch identical to the aforementioned one with added yeasts of the aforementioned two kinds, at 30° C. and pH 5.0-5.4 with stirring at 100 rpm for 4 days. The alcohol concentration in the aforementioned slurry liquefied/fermented for 3 days was 2.5 wt %, and the generated gas volume was 10.9 Nl/kg-slurry (carbon dioxide 97 vol %, hydrogen 2.5 vol %, others 0.5 vol %). The volume of slaked lime consumed for adjusting the pH during fermentation was 4.0 g/kg-slurry.

Next, 0.5 kg of the aforementioned liquefied slurry and 1.5 kg of the seed culture for gasification fermentation were charged into a 2l fermentation tank with specifications identical to the one which was used for the aforementioned liquefaction, and were subjected to a batchwise gasification fermentation with stirring at 70 rpm and at 60° C. and pH 7.6–7.8 for 10 days. The seed culture for gasification was prepared from garbage slurry of the batch identical to that of the aforementioned one with added middle-temperature gasification bacteria (middle-temperature methane bacteria) and the mixture thereof was charged into a 20l acrylic plastic fermentation tank for culturing under an anaerobic condition at 60° C. and pH 7.6–7.8 for over 1 month. The volumeof recovered gas at the end fermentation was 37.0 Nl/kg-slurry (methane purity 87 vol %), of which methane was 32.2 N l/kg-slurry and carbon dioxide 4.8 Nl/kg-slurry.

EXAMPLE 5

1.5 kg of garbage slurry from the batch identical to the one which was used for Example 2 (organics concentration 9.8 wt %) and 0.5 kg of liquefaction seed culture obtained by mix-cultuing in advance two kinds of yeasts of *Saccharomyces carlsbergensis* and *Candida lipolitica* were charged into a cylindrical acrylic plastic fermentation tank of a 2l capacity equipped with a stirrer, jacket and an automatic pH adjusting system and were subjected to a liquefaction fermentation treatment with stirring at 100 rpm and at 30° C. and pH 5.0–5.4 for 3 days. The aforementioned liquefaction seed culture was prepared by adding the aforementioned two kinds of yeast to 2 kg of garbage slurry from the batch identical to the aforementioned one and fermented with stirring at 100 rpm and at 30° C. and pH 5.0–5.4 for 4 days. The alcohol concentration in the slurry liquefied/fermented 3 days was 2.2 wt %, and the generated gas volume during fermentation was 10.7 Nl/kg-slurry (carbon dioxide 98 vol %, hydrogen 1.6 %, others 2.4 vol %). The volume of slaked lime required for pH adjustment was 2.4 g/kg-slurry.

Next, 0.5 kg of the aforementioned slurry after liquefaction treatment, together with 1.5 kg of seed culture for gasification, was charged into a 2l fermentation tank with the identical specifications as used for the aforementioned liquefaction treatment, and the mixture thereof underwent a batchwise gasification treatment with stirring at 70 rpm and at 60° C. and pH 7.6–7.8 for 10 days. The aforementioned seed culture for gasification was cultured by adding middle-temperature gasification bacteria (middle-temperature methane bacteria) to the garbage slurry of the batch identical to the aforementioned one and this mixture was charged into a 20l acrylic plastic fermentation tank wherein it was cultured under an anaerobic condition at 60° C. and pH 7.6–7.8 for over 1 month. The recovered gas volume at the end of fermentation was 35.0 Nl/kg-slurry (methane purity 90.5 vol %), of which methane and carbon dioxide were 32.6 Nl/kg-slurry and 3.4 N l/kg-slurry respectively.

EXAMPLE 6

1.5 kg of the garbage slurry from the batch identical to the one used for Example 2 (organics concentration 9.8 wt %) and 0.5 kg of liquefaction seed culture prepared in advance by culturing *Saccharomyces diastics* were charged into a cylindrical acrylic plastic fermentation tank of an 2l capacity equipped with a stirrer, jacket and a automatic pH adjusting system, and the mixture therein was subjected to a liquefaction fermentation with stirring at 100 rpm and at 30° C. and pH 5.0–5.4 for 3 days. The aforementioned seed culture was prepared by adding the aforementioned yeast to 2 kg of the garbage slurry from the batch identical to the aforementioned one and fermented at 30° C. and pH 5.0–5.4 with stirring at 100 rpm for 4 days. The alcohol concentration in the aforementioned slurry liquefied/fermented for 3 days was 2.1 wt % and the generated gas volume was 10.8 Nl/kg-slurry (carbon dioxide 97 vol %, hydrogen 2.6 vol %, others 0.4 vol %). The volume of slaked lime required for pH adjustment in the process of fermentation was 2.1 g/kg-slurry.

Next, into a 2l fermentation tank with the specifications identical to those of the tank used for the aforementioned liquefaction, 0.5 kg of the aforementioned liquefiled slurry and 1.5 kg of gasification fermentation seed culture were charged for a batchwise gasification fermentation at 60° C. and pH 7.6–7.8 with stirring at 70 rpm for 10 days. The gasification seed culture was prepared from the garbage slurry from the batch identical to the aforementioned one, which was charged into a 20l acrylic plastic fermentation tank together with middle-temperature gasification fermentation bacteria (middle-temperature methane bacteria) and was cultured under an anaerobic condition at 60° C. and pH 7.6–7.8 for over 1 month. The recovered gas volume at the end of fermentation was 35.6 N l/kg-slurry (methane purity 9.10 vol%), ofwhich methane and carbon dioxide were 32.6 Nl/kg-slurry respectively.

COMPARATIVE EXAMPLE 2

As a reference to compare with Examples 2 through 6 the following experiment was performed.

1.5 kg of the garbage slurry of the batch identical to the one used for the aforementioned Example 2 (organics concentration 9.8 wt %) and 0.5 kg of the seed culture of volatile fatty acid generating bacteria (liquefaction fermentation bacteria) which was mix-cultured in advance with the aforementioned garbage slurry under an anaerobic condition at 30° C. and pH 5.8 for 3 days were charged into a liquefaction tank having specifications identical to the one which was used in Example 2, nd the mixture therein was subjected to a liquefaction fermentation for 3 days with stirring of 100 rpm at 30° C. and pH 5.8. The aforementioned seed culture was prepared through fermentation treatment of 2 kg of the garbage slurry taken from the batch identical to the aforementioned one together with the aforementioned volatile fatty acid generating bacteria with stirring at 100 rpm and at 30° C. and pH 5.8 for 4 days. The concentration of volatile fatty acid in the aforementioned slurry liquefied/fermented 3 days was 2.2 wt % (n-butyric acid 1.2 wt %, acetic acid 1.1 wt %, other fat acids 0.1 wt %), and the generated gas volume was 12.9 Nl/kg-slurry (carbon dioxide 51 vol %, hydrogen 47 vol %, others 5 vol %). The volume of slaked lime consumed for pH adjustment during fermentation was 19.0 g/kg-slurry.

Next, into a 2l fermentation tank of identical specifications to that which was used for the aforementioned liquefaction treatment, 0.5 kg of the above liquefied slurry and 1.5 kg of gasification fermentation seed culture were charged and a batchwise gasification fermentation was performed at 30° C., pH 7.6–7.8 with stirring at 70 rpm for 10 days. As for the gasification seed culture, that which was used was prepared from the garbage slurry taken from the identical batch to the aforementioned one and adding thereto middle-temperature methane bacteria. The mixture thereof was charged into a 20l acrylic plastic fermentation tank wherein the mixture was cultured under an anaerobic condition at 30° C. and pH 7.6–7.8 for over 1 month. The gas generation volume in the course of 10 days of fermentation was 32.6 Nl/kg-slurry (methane purity 75.2 vol %), of which methane and carbon dioxide were 24.5 vol %/kg-slurry and 8.1 vol %/kg-slurry respectively.

In comparing the aforementioned Examples 2 through 6 with Comparative Example 2, it is clear that the recovered volume of methane was improved by 13% on the average as against Comparative Example 2, and at the same time the methane purity was improved to 89.6 vol/% on the average as against 75.2% in Comparative Example 2. Furtheremore, the volume of slaked line consumed for liquefaction fermentation per 1 kg of garbage slurry was reduced by 86% on the average as against Comparative Example 2.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A digestion process for treating starch containing garbage consisting essentially of the steps of:
   (a) subjecting said starch containing garbage to an alcohol producing anaerobic fermentation in the slurry state without sterilizing said starch containing garbage in the presence of at least one ethanol producing yeast which directly converts starch into ethanol without a hydrolysis pretreatment step,
   (b) subjecting the resultant alcohol fermented product containing ethanol directly to methane producing anaerobic fermentation in the presence of methane producing bacteria which directly converts ethanol into methane, and
   (c) recovering the methane generated by said methane producing anaerobic fermentation.

2. The digestion process according to claim 1, wherein at least one member selected from the group consisting of amylase producing yeasts, lipase producing yeasts and protease producing yeasts is mix-cultured with said ethanol-producing yeast during said alcohol producing anaerobic fermentation step.

3. The digestion process according to claim 2, wherein said mixcultured yeast is an amylase producing yeast selected from at least one member of the group consisting of *Endomycopsis fibuliger, Schizosaccharomyces pombe* and *Saccharomyces diastatics.*

4. The digestion process according to claim 2, wherein said mixcultured yeast is a lipase producing yeast selected from at least one member of the group consisting of *Candida cylindracea, Candida lipolitica* and *Trichosporen pullens.*

5. The digestion process according to claim 2, wherein said mix-cultured yeast is a protease producing yeast selected from at least one member of the group consisting of *Candida lipolitica* and *Candida parapsilosis.*

6. The digestion process according to claim 1, wherein said alcohol producing anaerobic fermentation step is performed under anaerobic conditions at a temperature within the range of from 20° C. to 40° C. and the pH within the range of from 4 to 6.5.

7. The digestion process according to claim 1, wherein said methane producing anaerobic fermentation step is conducted under anaerobic conditions at a temperature within the range of from 20° C. to 75° C. and the pH within the range of from 7 to 8.

8. The digestion process according to claim 1, wherein said ethanol producing yeast belongs to a genus selected from the group consisting of Saccharomyces, Schizosaccharomyces, Schwaniomyces, Torulopsis, Brettanomyces and Candida.

9. The digestion process according to claim 1, wherein said alcohol producing anaerobic yeast is an amylase producing yeast.

* * * * *